United States Patent
Dixon et al.

(10) Patent No.: US 12,076,431 B2
(45) Date of Patent: *Sep. 3, 2024

(54) COSMETIC COMPOSITIONS FOR COMBATTING COLOUR LOSS FROM A DYED MATERIAL

(71) Applicant: INNOSPEC LIMITED, Ellesmere Port (GB)

(72) Inventors: Nicholas John Dixon, Chester (GB); Matthew Robert Giles, Chester (GB); Kimberley Elizabeth Griffiths, Denbighshire (GB); Tony Gough, Chester (GB); Ian Malcolm McRobbie, Chester (GB)

(73) Assignee: Innospec Limited, Ellesmere Port (GB)

( * ) Notice: Subject to any disclaimer, the term of this patent is extended or adjusted under 35 U.S.C. 154(b) by 100 days.

This patent is subject to a terminal disclaimer.

(21) Appl. No.: 16/337,566

(22) PCT Filed: Sep. 29, 2017

(86) PCT No.: PCT/GB2017/052930
§ 371 (c)(1),
(2) Date: Mar. 28, 2019

(87) PCT Pub. No.: WO2018/060728
PCT Pub. Date: Apr. 5, 2018

(65) Prior Publication Data
US 2019/0231664 A1   Aug. 1, 2019

(30) Foreign Application Priority Data

Sep. 30, 2016 (GB) ..................................... 1616666
Sep. 30, 2016 (GB) ..................................... 1616670

(51) Int. Cl.
| | | |
|---|---|---|
| *A61K 8/44* | (2006.01) |
| *A61K 8/06* | (2006.01) |
| *A61K 8/33* | (2006.01) |
| *A61K 8/34* | (2006.01) |
| *A61K 8/36* | (2006.01) |
| *A61K 8/41* | (2006.01) |
| *A61K 8/49* | (2006.01) |
| *A61Q 5/00* | (2006.01) |
| *A61Q 5/04* | (2006.01) |
| *A61Q 5/06* | (2006.01) |
| *A61Q 5/12* | (2006.01) |

(52) U.S. Cl.
CPC ............... *A61K 8/44* (2013.01); *A61K 8/062* (2013.01); *A61K 8/33* (2013.01); *A61K 8/342* (2013.01); *A61K 8/361* (2013.01); *A61K 8/41* (2013.01); *A61K 8/442* (2013.01); *A61K 8/4913* (2013.01); *A61Q 5/00* (2013.01); *A61Q 5/002* (2013.01); *A61Q 5/004* (2013.01); *A61Q 5/04* (2013.01); *A61Q 5/06* (2013.01); *A61Q 5/12* (2013.01); *A61K 2800/51* (2013.01)

(58) Field of Classification Search
None
See application file for complete search history.

(56) References Cited

U.S. PATENT DOCUMENTS

| | | | | |
|---|---|---|---|---|
| 4,486,328 A | * | 12/1984 | Knott ..................... | A61K 8/361 510/123 |
| 5,246,613 A | * | 9/1993 | Gilbert ..................... | A61K 8/44 510/159 |
| 11,000,461 B2 | * | 5/2021 | Dixon ..................... | A61K 8/342 |
| 2004/0187226 A1 | | 9/2004 | Muerner et al. | |
| 2008/0159975 A1 | | 7/2008 | Nho et al. | |
| 2008/0313821 A1 | | 12/2008 | Lalleman et al. | |
| 2011/0086793 A1 | | 4/2011 | Smets et al. | |
| 2013/0174863 A1 | * | 7/2013 | Marsh ..................... | A61K 8/44 132/202 |
| 2015/0034117 A1 | | 2/2015 | Pressly et al. | |
| 2015/0034119 A1 | | 2/2015 | Pressly et al. | |
| 2019/0091121 A1 | | 3/2019 | Dixon et al. | |
| 2019/0216703 A1 | * | 7/2019 | Scheunemann .......... | A61Q 5/12 |
| 2019/0216714 A1 | * | 7/2019 | Scheunemann ........ | A61K 8/361 |
| 2019/0240129 A1 | * | 8/2019 | Scheunemann .......... | A61K 8/416 |
| 2020/0030203 A1 | * | 1/2020 | Scheunemann .......... | A61K 8/27 |
| 2020/0179254 A1 | * | 6/2020 | Scheunemann .......... | A61Q 5/02 |

FOREIGN PATENT DOCUMENTS

| | | |
|---|---|---|
| CN | 104758213 A | 7/2018 |
| EP | 0583534 A1 | 2/1994 |
| EP | 2005939 A1 | 12/2008 |
| FR | 2937543 A1 | 4/2010 |
| GB | 966488 A | 8/1964 |
| GB | 981825 A | 1/1965 |
| GB | 2552570 A | 1/2018 |
| GB | 2552571 A | 1/2018 |

(Continued)

OTHER PUBLICATIONS

Machine translation, WO 2002/030373, printed 2019 (Year: 2019).*
Machine translation, JP 2002-265411, printed 2020.*
Betterton et al. "Henry's Law constants of some environmentally important aldehydes," Environmental Science & Technology 22:1415-1418, 1988 (Year: 1988).*
Google translation JP 2006-137686 A, printed 2023 (Year: 2023).*
United Kingdom Search Report under Section 17(5) issued on Jun. 19, 2017 for Application No. GB1616670.4.
International Search Report and Written Opinion issued on Apr. 18, 2018 for Application No. PCT/GB2017/052930.

(Continued)

*Primary Examiner* — Ileana Popa
*Assistant Examiner* — Alissa Prosser
(74) *Attorney, Agent, or Firm* — Carlos A. Fisher; Stout, Uxa & Buyan, LLP

(57) ABSTRACT

A concentrate composition comprising: (a) at least 0.1 wt % of a surfactant compound; and (b) at least 10 wt % one or more ingredients selected from aldehydes, succinimidyl esters, chelating agents and amine salts of carboxylic acids.

7 Claims, No Drawings

(56) References Cited

FOREIGN PATENT DOCUMENTS

| | | | | |
|---|---|---|---|---|
| JP | 11199446 | A | | 7/1999 |
| JP | 11199448 | A | | 7/1999 |
| JP | 2002265411 | A | * | 9/2002 |
| JP | 22000-128747 | A | | 5/2005 |
| JP | 2006137686 | A | * | 6/2006 |
| JP | 2009263319 | A | | 11/2009 |
| WO | 2002030373 | A2 | | 4/2002 |
| WO | WO-0230373 | A2 | * | 4/2002 ............... A61K 8/33 |
| WO | 2004093541 | A1 | | 11/2004 |
| WO | 2009024938 | A2 | | 2/2009 |
| WO | 2015074971 | A1 | | 5/2015 |
| WO | WO-2017041907 | A1 | * | 3/2017 ............... A61K 8/19 |
| WO | WO-2018059765 | A1 | * | 4/2018 ............... A61K 8/26 |
| WO | WO-2018059778 | A1 | * | 4/2018 ............... A61K 8/44 |
| WO | WO-2018059779 | A1 | * | 4/2018 ........... A61K 8/4913 |
| WO | WO-2018059780 | A1 | * | 4/2018 ............ A61K 8/345 |
| WO | WO-2018059787 | A1 | * | 4/2018 ............... A61K 8/19 |

OTHER PUBLICATIONS

Database GNPD [Online] Mintel; Sep. 1, 2009 (Sep. 1, 2009 ), "Colour effect shampoo", Database accession No. 1182152.

Anonymous: "Super special shampoo", GNPO, Jul. 31, 2015 (Jul. 31, 2015), [retrieved on Jul. 31, 2015].

Verhovnik et al., "Silsoft A-553 Conditioning Agent and Silsoft A-454 Colour Retaining Conditioning Agent: New Dimethicone Conditioners For Hair Care" Euro-Cosme, Heidelberg, DE, No. 3, Jan. 1, 2002 (Jan. 1, 2002), pp. 20-25, XP009109558, ISSN: 0944-8942.

International Preliminary Report on Patentability issued on Apr. 11, 2019 for International Application No. PCT/ GB2017/052930.

Office Action Dated Dec. 11, 2020 in corresponding European Patent Application No. 17780186.7.

http://www.gnpd.com, Illuminating Color Protection Styling Products.

* cited by examiner

COSMETIC COMPOSITIONS FOR COMBATTING COLOUR LOSS FROM A DYED MATERIAL

CROSS-REFERENCE TO RELATED APPLICATIONS

This application is a U.S. national stage application under 35 U.S.C. 371 of co-pending International Application No. PCT/GB2017/052930, filed on Sep. 29, 2017, and entitled COSMETIC COMPOSITIONS FOR COMBATTING COLOUR LOSS FROM A DYED MATERIAL, which in turn claims priority to and benefit of Great Britain Patent Application No. 1616666.2, filed on Sep. 30, 2016 and Great Britain Patent Application No. 1616670.4, filed on Sep. 30, 2016 which are incorporated by reference herein in their entirety for all purposes.

The present invention relates to hair care compositions and to methods and uses relating thereto. The invention relates especially to compositions comprising more than one ingredient that may be useful for dosing into hair care formulations. In particular the composition relates to compositions useful in preventing or inhibiting the loss of colour from dyed hair.

Procedures for dyeing materials, especially hair and other keratinous materials, have been in existence for many years. However the dyed materials lose colour intensity and vibrancy after dyeing. One cause of this loss of colour is believed to be leaching of dye molecules from the materials when in contact with water or other solvents which can dissolve/solubilise the dyes and cause them to diffuse out of the material. This colour loss can thus occur during processes such as washing of the material (shampooing in the case of hair) or during other processes where the material comes into contact with water or other solvents that can leach dyes from the material. The problem is greater in the case of small dye molecules as these are more mobile and can thus be leached from the material at a faster rate than larger dye molecules. As a result, repeated washing of materials can lead to colour loss over time. This can also cause a colour shift, for example whereby one or more dye compounds present in a mixture used to colour a material are leached from the material to a greater extent than the others during washing.

For textile materials and fabrics colour loss can occur during washing of the material, either in a hand washing process or in an automatic washing machine.

One effective means by which colour loss can be prevented or inhibited is by treatment with formaldehyde. However formaldehyde is a suspected carcinogen and thus its use in cosmetic compositions is strictly regulated and highly undesirable. There have been numerous attempts to provide alternative means for combatting colour loss from hair. However to date none of these have been completely satisfactory and there therefore exists a need to develop further improved strategies.

A number of components have been found to be effective at reducing colour loss from dyed hair and it is therefore desirable to include these in hair care formulations such as shampoo, conditioners and styling products. However the addition of new components into formulations is not always straight forward and simply admixing an additional functional material with a formulated composition is often not successful.

The formulation of hair care and other personal care compositions is often complicated. The order in which components are added and how they are mixed may be important as it is often the case that emulsions are formed and changing the balance of ingredients can cause these to breakdown.

Hair care compositions typically contain a number of ingredients and each time a component is mixed into the composition a new process step has to be developed. Complex formulation processes are undesirable as these significantly increase the costs associated with production. It is therefore beneficial to include as few components as possible when formulating hair care products. As such components which contain multiple ingredients in a stable form are highly advantageous. It is also desirable that components for inclusion in hair care formulations do not contain excessive levels of water as this would then need to be removed, at a different point in the process.

The present inventors have developed a concentrated multiple ingredient composition for use in formulating hair care products.

According to a first aspect of the present invention there is provided a concentrate composition comprising:
  (a) at least 0.1 wt % of surfactant compound; and
  (b) at least 10 wt % of one or more further ingredients selected from aldehydes, succinimidyl esters, chelating agents and amine salts of a carboxylic acids.

The concentrate composition of the present invention comprises (a) a surfactant compound and one or more further ingredients (b). For the avoidance of doubt, the surfactant compound (a) is separate to and present in addition to the ingredients of component (b), which in some cases may have surface-active properties.

Component (a) comprises a surfactant compound. Any suitable surfactant compound may be used. The surfactant compound may be selected from anionic, cationic, nonionic and amphoteric surfactants. Suitable surfactants of these types will be known to the person skilled in the art.

Preferably component (a) is selected from anionic and amphoteric surfactants.

Suitable anionic surfactants for use in the composition of the present invention include salts of $C_{12}$ to $C_{18}$ carboxylic acids, ethoxylated carboxylic acids, ester carboxylates and ethoxylated ester carboxylates and sarcosinates. Other suitable anionic surfactants include sulfates and sulfonates, for example alkyl sulfates, alkyl ether sulfates, alcohol sulfates, alcohol ether sulfates, α-olefin sulfonates, linear alkyl sulfonates; and phosphate esters.

Suitable anionic surfactants may be selected from salts of fatty acids; alkali metal salts of mono- or dialkyl sulfates; mono- or dialkyl ether sulfates; lauryl ether sulfates; alkyl sulfonates; alkyl aryl sulfonates; primary alkane disulfonates; alkene sulfonates; hydroxyalkane sulfonates; alkyl glyceryl ether sulfonates; alpha-olefinsulfonates; alkyl phosphates; sulfonates of alkylphenolpolyglycol ethers; salts of alkyl sulfopolycarboxylic acid esters; alkyl sulfosuccinates and salts thereof, alkyl ether sulfosuccinates and salts thereof, non-acylated alkyl isethionates; fatty acid taurates; acyl taurates; products of condensation of fatty acids with oxy- and aminoalkanesulfonic acids; sulfated derivatives of fatty acids and polyglycols; alkyl and acyl sarcosinates; sulfoacetates; alkyl phosphates; alkyl phosphate esters; acyl lactates; alkanolamides of sulfated fatty acids and salts of lipoamino acids. Particularly exemplary salts of the above, where applicable, are the sodium, potassium, ammonium, magnesium and triethanolamine salts.

Preferred anionic surfactants for use herein include sodium laureth sulfate, sodium lauroyl methyl isethionate, sodium cocoyl methyl isethionate, sodium alpha-olefin sulfonate, sodium lauryl sulfoacetate, sodium monoalkyl phosphates, sodium dialkyl phosphates and sodium cocoyl methyl taurate.

One especially preferred anionic surfactant is sodium laureth sulfate.

Suitable amphoteric surfactants include those based on fatty nitrogen derivatives and those based on betaines.

Suitable amphoteric or zwitterionic surfactants may be selected from betaines, for example alkyl betaines, alkylamidopropyl betaines, alkylamidopropyl hydroxy sultaines, alkylampho acetates, alkylamphodiacetates, alkylamphopropionates, alkylamphodipropionates, alkyliminodipropionates and alkyliminodiacetate.

Amphoteric or zwitterionic surfactants for use in the compositions of the present invention may include those which have an alkyl or alkenyl group of 7 to 22 carbon atoms and comply with an overall structural formula:

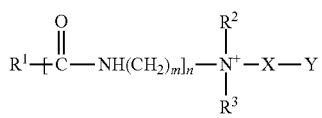

where $R^1$ is alkyl or alkenyl of 7 to 22 carbon atoms; $R^2$ and $R^3$ are each independently alkyl, hydroxyalkyl or carboxyalkyl of 1 to 6 carbon atoms; m is 2 to 4; n is 0 or 1; X is alkylene of 1 to 6 carbon atoms optionally substituted with hydroxyl; and Y is $-CO_2$ or $-SO_3$.

Amphoteric or zwitterionic surfactants may include simple betaines of formula:

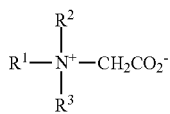

and amido betaines of formula:

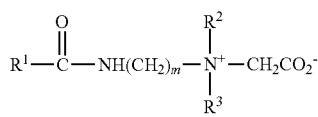

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters, of the groups $R^1$ has 10 to 14 carbon atoms. $R^2$ and $R^3$ are preferably methyl.

Amphoteric or zwitterionic surfactants may include sulphobetaines of formula:

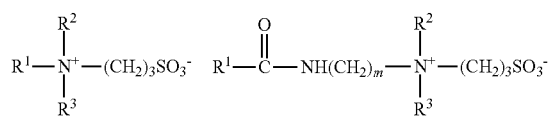

where m is 2 or 3, or variants of these in which $-(CH_2)_3SO_3^-$ is replaced by

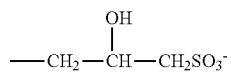

where $R^1$, $R^2$ and $R^3$ in these formulae are as defined previously.

Amphoteric or zwitterionic surfactants may include amphoacetates and diamphoacetates. Amphoacetates generally conform to the following formula:

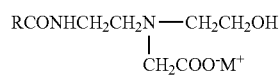

Diamphoacetates generally conform to the following formula:

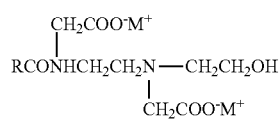

where R is an aliphatic group of 8 to 22 carbon atoms and M is a cation such as sodium, potassium, ammonium, or substituted ammonium.

Suitable acetate-based surfactants include lauroamphoacetate; alkyl amphoacetate; cocoampho(di)acetate; cocoamphoacetate; disodium cocoamphodiacetate; sodium cocoamphoacetate; disodium cocoamphodiacetate; disodium capryloamphodiacete; disodium lauroamphoacetate; sodium lauroamphoacetate and disodium wheatgermamphodiacetate.

Suitable betaine surfactants include alkylamido betaine; alkyl betaine, $C_{12/14}$ alkyldimethyl betaine; cocoamidopropylbetaine; tallow bis(hydroxyethyl) betaine; hexadecyldimethylbetaine; cocodimethylbetaine; alkyl amido propyl sulfo betaine; alkyl dimethyl amine betaine; coco amido propyl dimethyl betaine; alkyl amido propyl dimethyl amine betaine; cocamidopropyl betaine; lauryl betaine; laurylamidopropl betaine, coco amido betaine, lauryl amido betaine, alkyl amino betaine; alkyl amido betaine; coco betaine; lauryl betaine; diemethicone propyl PG-betaine; oleyl betaine; N-alkyldimethyl betaine; coco biguamide derivative, $C_8$ amido betaine; $C_{12}$ amido betaine; lauryl dimethyl betaine; alkylamide propyl betaine; amido betaine; alkyl betaine; cetyl betaine; oleamidopropyl betaine; isostearamidopropyl betaine; lauramidopropyl betaine; 2-alkyl-N-carboxymethyl-N-hydroxyethyl imidazolinium betaine; 2-alkyl-N-carboxyethyl-N-hydroxyethyl imidazolinium betaine; 2-alkyl-N-sodium carboxymethyl-N-carboxymethyl oxyethyl imidazolinium betaine; N-alkyl acid amidopropyl-N,N-dimethyl-N-(3-sulfopropyl)-ammonium-betaine; N-alkyl-N,N-dimethyl-N-(3-sulfopropyl)-ammonium-betaine; cocodimethyl betaine; apricotamidopropyl betaine; isostearamidopropyl betaine; myristamidopropyl betaine; palmitamidopropyl betaine; cocamidopropyl hydroxyl sultaine; undecylenamidopropyl betaine; cocoamidosulfobetaine; alkyl amido betaine; $C_{12/18}$ alkyl amido propyl dimethyl amine betaine; lauryldimethyl betaine; ricinol amidobetaine; tallow aminobetaine.

Preferred amphoteric surfactants for use herein include cocamidopropyl betaine, sodium lauroamphoacetate, cocamidopropylhydroxy sultaine and disodium cocoamphodiacetate.

One especially preferred amphoteric surfactant for use herein is cocamidopropyl betaine.

Component (a) may contain a mixture of components. Such mixtures are preferably selected from any of the anionic and amphoteric surfactants listed above.

Preferably component (a) is selected from sodium laureth sulfate, cocamidopropyl betaine and mixtures thereof.

Component (b) comprises one or more of ingredients selected from aldehydes, succinimidyl esters, chelating agents and amine salts of carboxylic acids.

Component (b) may comprise an aldehyde.

Preferred aldehydes for use herein include hydroxyl-substituted aldehydes and alpha-substituted aldehydes. Aldehydes with a hydroxy substituent at the α-position are especially preferred.

Suitable aldehydes for use herein have at least 2 carbon atoms. Preferably they have at least 3 carbon atoms.

Suitable aldehydes for use herein may have up to 36 carbon atoms, preferably up to 30 carbon atoms, more preferably up to 24 carbon atoms, preferably up to 20 carbon atom, for example up to 18 carbon atoms or up to 16 carbon atoms.

Some preferred aldehydes for use herein have from 3 to 20 carbon atoms, for example 3 to 16 carbon atoms.

Some preferred aldehydes for use herein have from 3 to 12 carbon atoms, for example 3 to 11 carbon atoms.

Some especially preferred aldehydes for use herein have from 3 to 9 carbon atoms, more preferably from 3 to 8 carbon atoms.

Some other preferred aldehydes for use herein have from 8 to 16 carbon atoms, for example 10 to 14 carbon atoms.

In some preferred embodiments the aldehyde contains only one aldehyde functional group.

The aldehyde preferably has a substituent at the α-position and/or has a hydroxy substituent. It may have one or more further substituents.

Suitable further substituents may be selected from a further hydroxy substituent, a further aldehyde group, a keto group, a carboxy group, an acyl group, a halo group, an alkoxy group, an alkyl group, a nitro group, an amino group, a sulfoxy group, a mercapto group, an amide, an ester, a nitrile group or an isonitrile group.

Preferred halo substituents are chloro, fluoro, and bromo.

Preferred alkoxy substituents are methoxy, ethoxy, propoxy and butoxy, including isomers thereof.

Preferred alkyl substituents are $C_1$ to $C_8$ alkyl, preferably $C_1$ to $C_6$ alkyl, including isomers thereof.

In some embodiments the aldehyde may include a further aldehyde functional group. Suitably such further aldehyde groups may be α-substituted.

In preferred embodiments the aldehyde includes a hydrocarbon chain. This is suitably a chain with a carbon backbone. However compounds in which the carbon backbone is interrupted by one or more heteroatoms are also within the scope of the invention. For example the carbon backbone may be interrupted by one or more oxygen, sulphur or nitrogen molecules and thus the aldehyde may include an ether, a thioether, an amine or a disulfide moiety.

The aldehyde may be predominantly aliphatic or predominantly aromatic in nature. Preferably the aldehyde is aliphatic. However it may include one or more double bonds and/or one or more cyclic groups. It may be straight-chain or branched.

In embodiments in which the aldehyde is hydroxy-substituted any suitable hydroxy substituted aldehyde may be included.

The aldehyde may comprise one or more hydroxy substituents.

Suitably the aldehyde comprises one, two or three hydroxy substituents, preferably one or two substituents.

In some preferred embodiments the aldehyde is not a saccharide.

Preferably the aldehyde comprises one hydroxy substituent.

Suitably the aldehyde has a hydroxyl substituent at the 2, 3 or 4 position.

In some embodiments the aldehyde may have a hydroxyl substituent at the 2 and 3 or the 2 and 4 positions.

Suitably the aldehyde may have a hydroxy substituent at the 2 position and/or the 3 position.

Suitably the aldehyde may have a hydroxy substituent at the 2 position or the 3 position.

In especially preferred embodiments the aldehyde has a hydroxy substituent at the 2 position. Thus the aldehyde is suitably an α-hydroxy aldehyde/a 2-hydroxy aldehyde.

The alpha-substituted aldehyde is suitably a compound of formula (I):

wherein X is selected from hydroxy, alkoxy, carboxy, alkylcarboxy, amino, nitro, mercapto, halo, keto, sulfoxy, alkyl, mercapto, amide, nitrile, isonitrile, ester and other carbonyl containing groups; Y is selected from hydrogen, hydroxy, alkoxy, carboxy, alkylcarboxy, amino, nitro, mercapto, halo, keto, sulfoxy, alkyl, mercapto, amide, nitrile, isonitrile, ester and other carbonyl containing groups; and R is hydrogen or an optionally substituted hydrocarbyl group having 1 to 36 carbon atoms.

In preferred embodiments Y is selected from hydrogen and a halogen. When Y is a halogen, X is suitably a halogen, for example X and Y may both be fluorine. In preferred embodiments Y is hydrogen.

Preferably the alpha-substituted aldehyde is a compound of formula (II):

wherein X is selected from hydroxy, alkoxy, carboxy, alkylcarboxy, amino, nitro, mercapto, halo, keto, sulfoxy, alkyl, mercapto, amide, nitrile, isonitrile, ester and other carbonyl containing groups and R is hydrogen, CHO or an optionally substituted hydrocarbyl group having 1 to 36 carbon atoms.

R may be hydrogen, CHO or an optionally substituted alkyl, alkenyl or aryl group having 1 to 30 carbon atoms, preferably 1 to 20 carbon atoms, more preferably 1 to 10 carbon atoms.

Suitably R may be hydrogen or an optionally substituted alkyl, alkenyl or aryl group having 1 to 30 carbon atoms, preferably 1 to 20 carbon atoms, more preferably 1 to 10 carbon atoms.

In some embodiments R is CHO and the aldehyde is a malondialdehyde derivative.

Preferably R is hydrogen or an optionally substituted alkyl or alkenyl group having 1 to 30, preferably 1 to 20, suitably 1 to 10 carbon atoms.

In some embodiments R is an optionally substituted alkyl or alkenyl group having 1 to 7, preferably 1 to 6 carbon atoms.

In some embodiments R is an optionally substituted alkyl or alkenyl group having 8 to 14, preferably 8 to 12 carbon atoms.

R may be substituted with one or more substituents selected from keto, hydroxyl, halo, carboxy, acyl, nitro, amino, mercapto, alkoxy, sulfoxy, ester, nitrile, isonitrile or amide. The carbon backbone may be interrupted by one or more heteroatoms, for example one or more oxygen, nitrogen or sulfur atoms.

In some preferred embodiments R is an unsubstituted alkyl group having 1 to 8, preferably 1 to 6 carbon atoms.

In some preferred embodiments R is an unsubstituted alkyl group having 4 to 16, preferably 8 to 12 carbon atoms.

R may be selected from hydroxy methylene, methyl, butyl, hexyl, octyl, decyl and dodecyl. These groups may be straight-chained or branched. Preferably they are straight-chained.

Suitably R is selected from hydrogen, hydroxymethylene, methyl, n-butyl and n-hexyl.

R may be selected from methyl, n-butyl, n-hexyl n-octyl, n-decyl and n-dodecyl.

Preferably R is selected from methyl, n-butyl and n-hexyl.

Most preferably R is selected from n-butyl and n-hexyl.

X is selected from hydroxy, alkoxy, carboxy, alkylcarboxy, amino, nitro, mercapto, halo, keto, sulfoxy, alkyl, mercapto, amide, nitrile, isonitrile, ester and other carbonyl containing groups.

In some preferred embodiments X is a group of formula OZ wherein Z is H, $R^1$, $R^3COR^2$, $R^3CONHR^2$, $R^3NHCOR^2$, $R^3OCOR^2$, or $R^3COOR^2$ wherein each of $R^1$ and $R^2$ is an optionally substituted hydrocarbyl group having 1 to 20 carbon atoms, preferably 1 to 8 carbon atoms, preferably 1 to 6 carbon atoms and most preferably 1 to 4 carbon atoms; and $R^3$ is a bond or an alkylene group having 1 to 20 carbon atoms, preferably 1 to 8 carbon atoms, preferably 1 to 6 carbon atoms and most preferably 1 to 4 carbon atoms.

$R^1$ and $R^2$ are optionally substituted alkyl groups. Preferred substituents are hydroxyl groups, especially terminal hydroxyl groups.

Suitably $R^1$ and $R^2$ are alkyl groups, preferably $C_1$ to $C_4$ alkyl groups.

In some especially preferred embodiments Z is H or $R^1$ wherein $R^1$ is a $C_1$ to $C_4$ alkyl group or a group of formula $HO(CH_2)_n$ wherein n is 1 to 6, preferably 1 to 4, preferably 2 or 3.

In some preferred embodiments X is a halo group. Suitably X is F, Br or Cl, preferably Br.

In some especially preferred embodiments X is selected from OH, $O(CH_2)_nA$, Cl, Br or F wherein n is from 1 to 6, preferably 1 to 4 and A is H or OH.

In some preferred embodiments X is $HOCH_2CH_2$ and R is hydrogen.

In some preferred embodiments X is Br and R is CHO.

In some most preferred embodiments X is OH and the aldehyde is a 2-hydroxy aldehyde.

In some preferred embodiments X is OH and R is a $C_1$ to $C_6$ alkyl or hydroxyalkyl group.

The compound of formula (II) is an aldehyde which is substituted at the 2 position. It may have one or more further substituents.

Suitable further substituents may be selected from a hydroxyl substituent, a further aldehyde group, a keto group, a carboxy group, an acyl group, a halo group, an alkoxy group, an alkyl group, a nitro group, an amino group, a sulfoxy group, a mercapto group, an amide, an ester, a nitrile group or an isonitrile group.

Preferred halo substituents are chloro, fluoro, and bromo.

Preferred alkoxy substituents are methoxy, ethoxy, propoxy and butoxy, including isomers thereof.

Preferred alkyl substituents are $C_1$ to $C_8$ alkyl, preferably $C_1$ to $C_6$ alkyl, including isomers thereof.

In some embodiments the aldehyde may include a further aldehyde functional group. Such further aldehyde groups may be α-substituted.

In preferred embodiments the aldehyde includes a hydrocarbon chain. This is suitably a chain with a carbon backbone. However compounds in which the carbon backbone is interrupted by one or more heteroatoms are also within the scope of the invention. For example the carbon backbone may be interrupted by one or more oxygen, sulfur or nitrogen molecules and thus the aldehyde may include an ether, a thioether, an amine or a disulfide moiety.

The aldehyde may be predominantly aliphatic or predominantly aromatic in nature. Preferably the aldehyde is aliphatic. However it may include one or more double bonds and/or one or more cyclic groups. It may be straight-chain or branched.

Suitable aldehydes for use herein include 2-hydroxydecanal, 2-hydroxydodecanal, 2-hydroxytetradecanal, 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde, 2-(2-hydroxyethoxy)acetaldehyde, 2-chloro octanal, 2-fluoro octanal, 2-bromo octanal, 6-hydroxyhexanal, 3-hydroxypropanal and 4-hydroxy-but-2-enal.

Suitable alpha-substituted aldehydes for use herein include hydroxydecanal, 2-hydroxydodecanal, 2-hydroxytetradecanal, 2-hydroxyhexanal, 2-hydroxyoctanal, 2-hydroxypropanal, glyceraldehyde, 2-hydroxybutanal, bromomalonaldehyde, 2-(2-hydroxyethoxy)acetaldehyde, 2-chloro octanal, 2-fluoro octanal and 2-bromo octanal.

Suitable alpha-substituted aldehydes for use herein include 2-hydroxyhexanal, 2-hydroxyoctanal, 2-hydroxypropanal, glyceraldehyde, 2-hydroxybutanal, bromomalonaldehyde, 2-(2-hydroxyethoxy)acetaldehyde, 2-chloro octanal, 2-fluoro octanal and 2-bromo octanal.

Suitable hydroxy-substituted aldehydes for use herein include-hydroxydecanal, 2-hydroxydodecanal, 2-hydroxytetradecanal, 2-hydroxyhexanal, 2-hydroxyoctanal, 2-hydroxypropanal, glyceraldehyde, 6-hydroxyhexanal, 3-hydroxypropanal, 4-hydroxy-but-2-enal, 2-hydroxybutanal, 3-hydroxybutanal and 4-hydroxybutanal.

Preferred hydroxy-substituted aldehydes for use herein include 2-hydroxyhexanal, 2-hydroxyoctanal, 2-hydroxypropanal, glyceraldehyde, 6-hydroxyhexanal, 3-hydroxypropanal, 4-hydroxy-but-2-enal, 2-hydroxybutanal, 3-hydroxybutanal and 4-hydroxybutanal.

Preferred alpha-hydroxy substituted aldehydes for use herein include 2-hydroxyhexanal, 2-hydroxyoctanal, 2-hydroxypropanal, glyceraldehyde, 2-hydroxybutanal, bromomalonaldehyde and 2-(2-hydroxyethoxy)acetaldehyde.

More preferred aldehydes for use herein include 2-hydroxyhexanal, 2-hydroxyoctanal, 2-hydroxypropanal and glyceraldehyde.

Most preferred hydroxy-substituted aldehydes for use herein are 2-hydroxyhexanal and 2-hydroxyoctanal and 2-hydroxypropanal.

In some embodiments component (b) comprises a mixture of two or more aldehydes.

In some embodiments component (b) comprises 2-hydroxyoctanal and one or more further aldehydes.

In some embodiments component (b) comprises glyceraldehyde and one or more further aldehydes.

In some embodiments component (b) comprises 2-hydroxyoctanal and glyceraldehyde. It may optionally comprise one or more further aldehydes.

In some embodiments component (b) comprises a first aldehyde having less than 10 carbon atoms and a second aldehyde having 10 or more carbon atoms. It may optionally comprise one or more further aldehydes. For example component (b) may comprises a first alpha-substituted aldehyde having 3 to 9 carbon atoms, preferably 3 to 8 carbon atoms and a second aldehyde having 10 to 18 carbon atoms, preferably 10 to 16 carbon atoms, more preferably 10 to 14 carbon atoms. Component (b) may optionally comprise one or more further aldehydes.

In some embodiments component (b) comprises one or more aldehydes selected from 2-hydroxydecanal, 2-hydroxydodecanal and 2-hydroxytetradecanal and one or more further aldehydes selected from 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde, 2-(2-hydroxyethoxy)acetaldehyde, 2-chloro octanal, 2-fluoro octanal, 2-bromo octanal, 6-hydroxyhexanal, 3-hydroxypropanal and 4-hydroxy-but-2-enal.

In some embodiments component (b) may comprise one or aldehydes selected from 2-hydroxydecanal, 2-hydroxydodecanal and 2-hydroxytetradecanal and one or more further aldehydes selected from 2-hydroxyhexanal, 2-hydroxyoctanal, 2-hydroxypropanal and glyceraldehyde.

Component (b) may comprise a succinimidyl ester.

Suitable succinimidyl esters include the compounds described in FR2937543.

Preferred succinimidyl esters include esters of monocarboxylic acids and esters of dicarboxylic acids.

Suitable succinimidyl esters of dicarboxylic acids include compounds of formula (III):

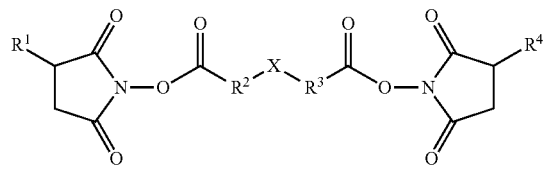

(III)

wherein each of $R^1$ and $R^4$ is independently hydrogen or a sulfonate moiety; each of $R^2$ and $R^3$ is independently a bond or an optionally substituted alkylene, alkenylene or arylene group and X is selected from a bond, $(CH_2)_n$, O, S or S—S.

$R^1$ is hydrogen or a sulfonate moiety. By sulfonate moiety we mean to refer to a group of formula $SO_3X$ where X is hydrogen, an alkali metal or ammonium ion. Preferably $R^1$ is hydrogen.

$R^4$ is hydrogen or a sulfonate moiety. By sulfonate moiety we mean to refer to a group of formula $SO_3X$ where X is hydrogen, an alkali metal or ammonium ion. Preferably $R^4$ is hydrogen.

$R^2$ is a bond or an optionally substituted alkylene, alkenylene or arylene group. It may be substituted with one or more substituents selected from keto, hydroxyl, halo, carboxy, acyl, nitro, amino, mercapto, alkoxy, sulfoxy, ester, nitrile, isonitrile or amide.

Preferably $R^2$ is an optionally substituted alkylene group. More preferably $R^2$ is an unsubstituted alkylene group.

$R^2$ may be straight chain or branched. Preferably $R^2$ has 1 to 12, more preferably 1 to 18, suitably 1 to 6, preferably 1 to 4, for example 1 or 2 carbon atoms.

$R^3$ is a bond or an optionally substituted alkylene, alkenylene or arylene group. It may be substituted with one or more substituents selected from keto, hydroxyl, halo, carboxy, acyl, nitro, amino, mercapto, alkoxy, sulfoxy, ester, nitrile, isonitrile or amide.

Preferably $R^3$ is an optionally substituted alkylene group. More preferably $R^3$ is an unsubstituted alkylene group.

$R^3$ may be straight chain or branched. Preferably $R^3$ has 1 to 12, more preferably 1 to 18, suitably 1 to 6, preferably 1 to 4, for example 1 or 2 carbon atoms.

X is a selected from a bond, $(CH_2)_n$, O, S or S—S. n is preferably from 1 to 10, for example from 1 to 4.

Preferably X is selected from S and S—S.

Some preferred diesters for use herein include the following compounds:

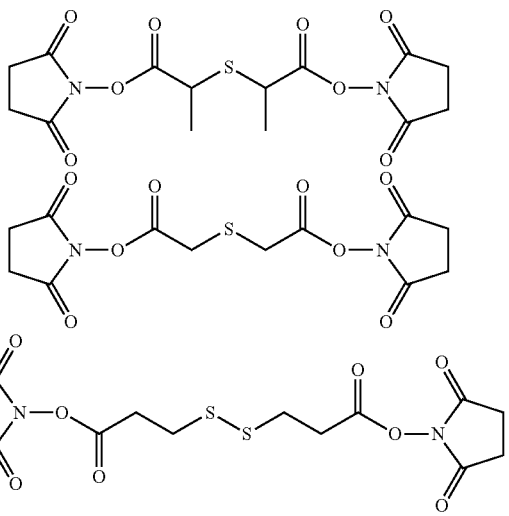

Preferred succinimidyl esters for use herein are esters of monocarboxylic acids.

Especially preferred succinimidyl esters for use herein include compounds of formula (IV):

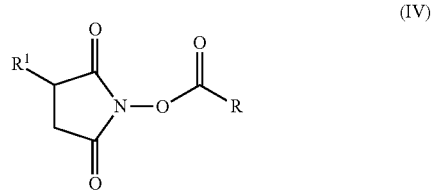

(IV)

wherein R is optionally substituted hydrocarbyl group having at least 5 carbon atoms; and $R^1$ is hydrogen or a solubilising agent.

$R^1$ is hydrogen or a solubilising group.

The solubilising group may be selected from any moiety which improves the water solubility of the compound of formula (I). Suitable solubilising group include hydroxy, alkoxy, polyalkoxy, alkylcarboxy, sulfo and phosphono groups.

Preferably $R^1$ is selected from hydrogen and a sulfonate moiety.

In some embodiments $R^1$ is a sulfonate moiety. By sulfonate moiety we mean to refer to a group of formula $SO_3X$ where X is hydrogen, an alkali metal or ammonium ion.

Preferably $R^1$ is hydrogen.

Preferably R is an optionally substituted hydrocarbyl group having up to 36 carbon atoms, suitably up to 30 carbon atoms, preferably up to 24 carbon atoms, more preferably up to 20 carbon atoms, preferably up to 18 carbon atoms, more preferably up to 14 carbon atoms and most preferably up to 12 carbon atoms.

R may be an optionally substituted alkyl, alkenyl, aryl, alkaryl or aralkyl group having 5 to 36 carbon atoms, suitably up to 5 to 30 carbon atoms, preferably 5 to 20 carbon atoms, more preferably 5 to 12 carbon atoms.

In some embodiments R is an aryl group having 6 to 24, preferably 6 to 16, more preferably 6 to 10 carbon atoms.

In some embodiments R is an optionally substituted phenyl group. R may be phenyl.

In some embodiments R is an optionally substituted alkyl or alkenyl group having 5 to 24, preferably 5 to 16, suitably 6 to 10 carbon atoms.

R may be substituted with one or more substituents selected from keto, hydroxyl, halo, aryl, carboxy, acyl, nitro, amino, mercapto, alkoxy, sulfoxy, ester, nitrile, isonitrile or amide. The carbon backbone may be interrupted by one or more heteroatoms, for example one or more oxygen, nitrogen or sulfur atoms.

In some preferred embodiments R is an unsubstituted alkyl group having 5 to 11, preferably 6 to 10, more preferably 7 to 9 carbon atoms.

Suitably R is selected from n-heptyl and n-nonyl.

Preferably R is n-heptyl.

Component (b) may comprise two or more succinimidyl esters.

Component (b) may further comprise a chelating agent.

Any suitable chelating agent may be used. Compounds of this type will be known to those skilled in the art.

Preferred chelating agents for use herein are polycarboxylic acid derived chelating agents.

The composition used in the present invention comprises a chelating agent. In some preferred embodiments the chelating agent is selected from glutamic acid N,N-diacetic acid (GLDA), diethylene triamine pentaacetic acid (DTPA), imido disuccinic acid (IDS), L-aspartic acid, diacetic acid (ASDA), ethylene diamine tetraacetic acid (EDTA), ethylene diamine disuccinic acid (EDDS), hydroxyethyl ethylenediaminetriacetic acid (HEDTA), citric acid and mixtures thereof.

The chelating agents used in the present invention are derivatives of polycarboxylic acids. By this we mean that the chelating agent includes two or more carboxylic acid moieties or salts thereof. Suitably chelating agents for use therein may include 3, 4 or 5 carboxylic acid moieties.

Glutamic acid N,N-diacetic acid (GLDA) has the structure shown below:

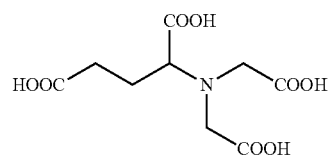 [SMILES: O=C(O)CCC(C(=O)O)N(CC(=O)O)CC(=O)O]

In the compositions of the present invention GLDA, may be present having the structure shown above and/or the same structure in which a number of the acidic protons have been replaced, i.e. in which 1, 2, 3 or 4 of the acid groups have been neutralised or partially neutralised. It may be present as a free acid or a salt or complex thereof.

GLDA may be present as either enantiomer or a mixture thereof. Preferably at least 50% is present as [S]-GLDA, preferably at least 70%, more preferably at least 90%, most preferably at least 95 wt %, for example about 98 wt %. In some preferred embodiments the GLDA consists essentially of the S enantiomer.

GLDA is commercially available as a solution comprising 38 wt % of the tetrasodium salt and is sold under the trade mark Dissolvine GL-38.

Diethylene triamine pentaacetic acid (DTPA) has the structure shown below:

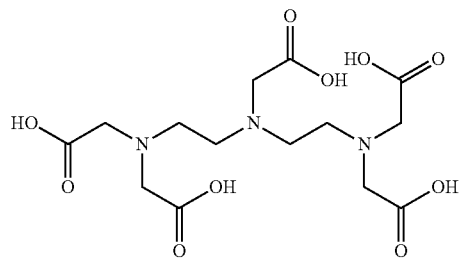 [SMILES: O=C(O)CN(CCN(CC(=O)O)CC(=O)O)CCN(CC(=O)O)CC(=O)O]

When component (b) comprises DTPA, this may be provided in a form having the structure shown above or in a form having the same structure in which a number of the hydrogen atoms have been replaced. Thus component (b) may comprise salts in which 1, 2, 3, 4 or 5 of the acid groups have been neutralised or partially neutralised.

When a salt of DTPA is included, this may be the salt of an alkali metal, an alkaline earth metal, ammonia or a suitable amine.

When a monovalent counterion is used the salt may be the monosalt, the disalt, the trisalt, the tetra salt or the pentasalt. For a divalent cation the monosalt or disalt may be present. Mixed salts may also exist, for example, the disodium magnesium salt or the sodium magnesium salt may be present. Preferably the counterion(s) to the DTPA residue is/are selected from one or more of sodium, magnesium, calcium, potassium, lithium, ammonium, and a quaternary ammonium ion.

Preferably DTPA when present is included as the pentasodium salt.

Iminodisuccinic acid (IDS) has the structure shown below:

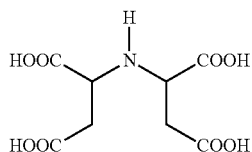

In the compositions of the present invention IDS may be present having the structure shown above and/or the same structure in which a number of the acidic protons have been replaced, i.e. in which 1, 2, 3 or 4 of the acid groups have been neutralised or partially neutralised. It may be present as a free acid or a salt or complex thereof.

IDS or a salt thereof may be present as either enantiomer or a mixture thereof. Preferably it is present as a racemic mixture.

IDS is commercially available as a solution comprising 34 wt % of the tetrasodium salt and is sold under the trade mark Baypure CX100.

ASDA is a structural isomer of IDS and has the structure shown below:

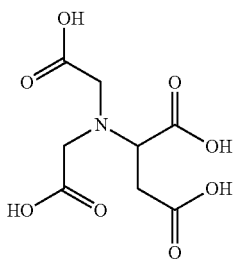 [SMILES: O=C(O)CC(C(=O)O)N(CC(=O)O)CC(=O)O]

In the compositions of the present invention ASDA may be present having the structure shown above and/or the same structure in which a number of the acidic protons have been replaced, i.e. in which 1, 2, 3 or 4 of the acid groups have been neutralised or partially neutralised. It may be present as a free acid or a salt or complex thereof.

EDTA has the structure shown below:

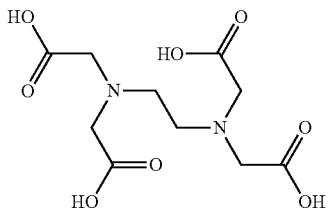 [SMILES: O=C(O)CN(CCN(CC(=O)O)CC(=O)O)CC(=O)O]

When component (b) comprises EDTA, this may be provided in a form having the structure shown above or in a form having the same structure in which a number of the hydrogen atoms have been replaced. Thus component (b) may comprise salts in which 1, 2, 3 or 4 of the acid groups have been neutralised or partially neutralised.

When a salt of EDTA is included, this may be the salt of an alkali metal, an alkaline earth metal, ammonia or a suitable amine.

When a monovalent counterion is used the salt may be the monosalt, the disalt, the trisalt or the tetrasalt. For a divalent cation the monosalt or disalt may be present. Mixed salts may also exist, for example, the disodium magnesium salt or the sodium magnesium salt may be present. Preferably the counterion(s) to the EDTA residue is/are selected from one or more of sodium, magnesium, calcium, potassium, lithium, ammonium, and a quaternary ammonium ion.

Preferably EDTA when present is present as the tetrasodium salt.

Ethylenediamine disuccinic acid (EDDS) which has the structure shown below:

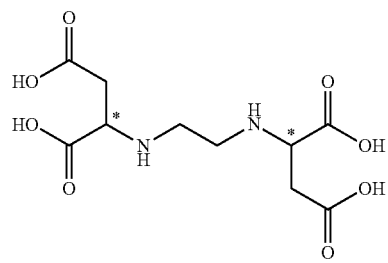 [SMILES: O=C(O)CC(NCCNC(CC(=O)O)C(=O)O)C(=O)O]

EDDS includes two stereogenic centres and there are three possible stereoisomers. A particularly preferred configuration is [S,S]-ethylenediamine disuccinic acid which is readily biodegradable.

In the compositions of the present invention "EDDS" may be present having the structure shown above and/or the same structure in which a number of the hydrogen atoms have been replaced. Thus EDDS may also contain succinate salts in which 1, 2, 3 or 4 of the acid groups have been neutralised or partially neutralised. It may be present as a free acid or a salt or complex thereof.

One commercially available material is trisodium ethylenediamine disuccinate. The commercial product (Natrlquest E30®) is supplied as an aqueous solution comprising 30% by weight [S,S] EDDS (expressed as free acid), or 37 wt % of the trisodium salt (including the counterion).

Another commercially available form of EDDS is the tetra acid, sold under the trade mark Natrlquest E80. This is provided as a powder which contains 80 wt % solid [S,S] EDDS as an acid, and water of crystallisation.

Hydroxyethylethylenediaminetriacetic acid (known as HEEDTA or HEDTA) has the structure shown below:

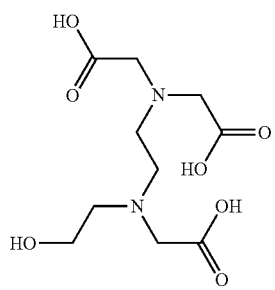 [SMILES: O=C(O)CN(CCO)CCN(CC(=O)O)CC(=O)O]

In the compositions of the present invention HEDTA may be present having the structure shown above and/or the same structure in which a number of the acidic protons have been replaced, i.e. in which 1, 2 or 3 of the acid groups have been neutralised or partially neutralised. It may be present as a free acid or a salt or complex thereof.

HEDTA is commercially available from Akzo Nobel as the trisodium salt under the trade mark Dissolvine H40.

Citric acid may be included as the free acid or as an alkali metal or ammonium salt.

In some preferred embodiments the chelating agent is selected from DTPA, GLDA, IDS and mixtures thereof.

In some especially preferred embodiments the chelating agent is selected from DTPA, GLDA and mixtures thereof.

Component (b) may comprise a mixture of chelating agents, suitably a mixture of polycarboxylic acid derived chelating agents.

Component (b) may comprise an amine salt of a carboxylic acid.

Suitable carboxylic acids include monocarboxylic acids, dicarboxylic acids and polycarboxylic acids.

Monocarboxylic acids are preferred.

In preferred embodiments the carboxylic acid includes a hydrocarbon chain. This is suitably a chain with a carbon backbone. However compounds in which the carbon backbone is interrupted by one or more heteroatoms are also within the scope of the invention. For example the carbon backbone may be interrupted by one or more oxygen, sulphur or nitrogen molecules and thus the carboxylic acid may include an ether, a thioether, an amine or a disulfide moiety.

The carboxylic acid may be predominantly aliphatic or predominantly aromatic in nature. Preferably the carboxylic acid is aliphatic. However it may include one or more double bonds and/or one or more cyclic groups. It may be straight-chain or branched.

In some especially preferred embodiments the salt is of a carboxylic acid of formula RCOOH, wherein R is an optionally substituted hydrocarbyl group, suitably an optionally substituted alkyl, alkenyl or aryl group.

In some embodiments R may have up to 40 carbon atoms, preferably up to 30 carbon atoms, more preferably up to 24 carbon atoms, suitably up to 18 carbon atoms, for example up to 12 carbon atoms.

In preferred embodiments the composition comprises a salt of an amine and a carboxylic acid having 4 to 10 carbon atoms.

Some preferred carboxylic acids have from 5 to 9 carbon atoms, for example 6 to 8 carbon atoms.

R may be an optionally substituted alkyl, alkenyl or aryl group having 3 to 9 carbon atoms, preferably 4 to 8 carbon atoms, more preferably 5 to 7 carbon atoms.

Preferably R is an optionally substituted alkyl or alkenyl group having 3 to 9, preferably 4 to 8, suitably 5 to 7 carbon atoms.

R may be substituted with one or more substituents selected from keto, hydroxyl, halo, carboxy, acyl, nitro, amino, mercapto, alkoxy, sulfoxy, ester, nitrile, isonitrile or amide. The carbon backbone may be interrupted by one or more heteroatoms, for example one or more oxygen, nitrogen or sulfur atoms.

Preferably R is a straight chain alkyl group.

In some preferred embodiments R is an unsubstituted alkyl group having 3 to 9, preferably 4 to 8, more preferably 5 to 7 carbon atoms.

Suitably R is selected from propyl, butyl, pentyl, hexyl, heptyl, cetyl, nonyl, including isomers and mixtures thereof.

Preferably R is selected from n-pentyl and n-heptyl.

Most preferably R is n-heptyl.

Component (b) may include the salt of a carboxylic acid and an amine.

Any suitable amine may be used to form the salt. Suitable amines include primary, secondary and tertiary amines, and ammonia.

In some preferred embodiments the amine is an alkylamino and/or hydroxyalkyl amino compound of formula $R^1R^2R^3N$, wherein each of $R^1$, $R^2$ and $R^3$ is hydrogen or an alkyl group or a hydroxyalkyl group. Each of $R^1$, $R^2$ and $R^3$ may be the same or different. Suitably each of $R^1$, $R^2$ and $R^3$ is independently selected from hydrogen and an alkyl or hydroxyalkyl group having 1 to 6 carbon atoms, for example 1 to 4 carbon atoms. Each of $R^1$, $R^2$ and $R^3$ may be independently selected from hydrogen, methyl, ethyl, propyl, butyl, pentyl, hexyl, hydroxymethyl, hydroxyethyl, hydroxypropyl, hydroxybutyl, hydroxypentyl, hydroxyhexyl and isomers thereof. The amine may be an alkylamine, a hydroxyalkylamine, a dialkylamine, a hydroxyalkyl alkyl amine, a dihydroxyalkylamine, a trialkylamine, a dialkylhydroxyalkylamine, a dihydroxyalkylamine or a trihydroxyalkylamine. There are many different compounds of this type and these will be known to the person skilled in the art.

In some embodiments the amine is a cyclic amine.

In some embodiments the amine is a primary amine. Suitable primary amines include methylamine, ethylamine, propylamine, butylamine, pentylamine, hexylamine. 2-aminobutanol, ethanolamine, cyclohexylamine, aminopropanediol, isopropanolamine, mixed isopropanolamines, tromethamine and benzylamine.

Preferably the amine is a secondary amine or a tertiary amine.

Suitable secondary amine compounds for use herein include dimethylamine, N,N-methylethylamine, N,N-methylpropylamine, N,N-methylbutylamine, diethylamine, N,N-ethylpropylamine, N,N-ethylbutylamine, dipropylamine, N,N-propylbutylamine, dibutylamine, N,N-butylmethylamine, N,N-butylethylamine, N,N-butylpropylamine, N,N-methylmethanolamine, N,N-methylethanolamine, diethanolamine, N,N-methylpropanolamine, dipropanolamine, N,N-methylbutanolamine, dibutanolamine, N,N-ethylmethanolamine, N,N-ethylethanolamine, N,N-ethylpropanolamine, N,N-ethylbutanolamine, N,N-propylmethanolamine, N,N-propylethanolamine, N,N-propylpropanolamine, N,N-propylbutanolamine, N,N-butylmethanolamine, N,N-butylethanolamine, N,N-butylpropanolamine, N,N-butylbutanolamine, 2-(2-aminoethoxy)ethanol, aminoethyl propanediol, aminomethyl propanediol, aminoethyl propanol, diisopropylamine, diisopropanolamine, morpholine and mixtures and isomers thereof.

Some preferred tertiary amine compounds for use herein include trimethylamine, N,N-dimethylethylamine, N,N-dimethylpropylamine, N,N-dimethylbutylamine, triethylamine, N,N-diethylmethylamine, N,N-diethylpropylamine, N,N-diethylbutylamine, tripropylamine, N,N-dipropylmethylamine, N,N-dipropylethylamine, N,N-dipropylbutylamine, tributylamine, N,N-dibutylmethylamine, N,N-dibutylethylamine, N,N-dibutylpropylamine, N,N-dimethylmethanolamine, methyldimethanolamine, N,N-dimethylethanolamine, methyldiethanolamine, N,N-dimethylpropanolamine, methyldipropanolamine, N,N-dimethylbutanolamine, methyldibutanolamine, N,N-diethylmethanolamine, ethyldimethanolamine, N,N-diethylethanolamine, ethyldiethanolamine, N,N-diethylpropanolamine, ethyldipropanolamine, N,N-diethylbutanolamine, ethyldibutanolamine, N,N-dipropylmethanolamine, propyldimethanolamine, N,N-dipropylethanolamine, propyldiethanolamine, N,N-dipropylpropanolamine, propyldipropanolamine, N,N-dipropylbutanolamine, propyldibutanolamine, N,N-dibutylmethanolamine, butyldimethanolamine, N,N-dibutylethanolamine, butyldiethanolamine, N,N-dibutylpropanolamine, butyldipropanolamine, N,N-dibutylbutanolamine, butyldibutanolamine, trimethanolamine, triethanolamine, tripropanolamine, tributanolamine, diethylhexylamine, dimethyltolylamine, bis-hydroxyethyl tromethamine, diethylethanolamine, dimethylamino methylpropanol, dimethyl isopropanolamine, dimethyl MEA, hydroxyethyl methyl tolyl amine, triisopropanolamine, bis-tris (2-[bis(2-hydroxyethyl)amino]-2-(hydroxymethyl)propane-1,3-diol]) and mixtures and isomers thereof.

In some embodiments the amine may be a diamine, a triamine or a polyamine, having two three or more nitrogen atoms. However preferred amines are monoamines or diamines, especially monoamines. When the amine is a diamine the salt may be a monosalt in which there is only one mole of acid per amine or a disalt in which there are two moles of acid per amine.

Suitable polyamines include polyalkylene polyamines.

Preferred diamines are optionally substituted alkylene diamines, for example ethylene diamines. Thus the amine may be an ethylene diamine of formula $R^1R^2NCH_2CH_2NR^3R^4$ wherein each of each of $R^1$, $R^2$, $R^3$ and $R^4$ is hydrogen or an alkyl group or a hydroxyalkyl group. Each of $R^1$, $R^2$, $R^3$ and $R^4$ may be the same or different. Suitably each $R^1$, $R^2$, $R^3$ and $R^4$ is independently selected from hydrogen and an alkyl or hydroxyalkyl group having 1 to 6 carbon atoms, for example 1 to 4 carbon atoms. Each of $R^1$, $R^2$, $R^3$ and $R^4$ may be independently selected from hydrogen, methyl, ethyl, propyl, butyl, pentyl, hexyl, hydroxymethyl, hydroxyethyl, hydroxypropyl, hydroxybutyl, hydroxypentyl and hydroxyhexyl.

Some especially preferred salts for use herein include the compounds having the following structures.

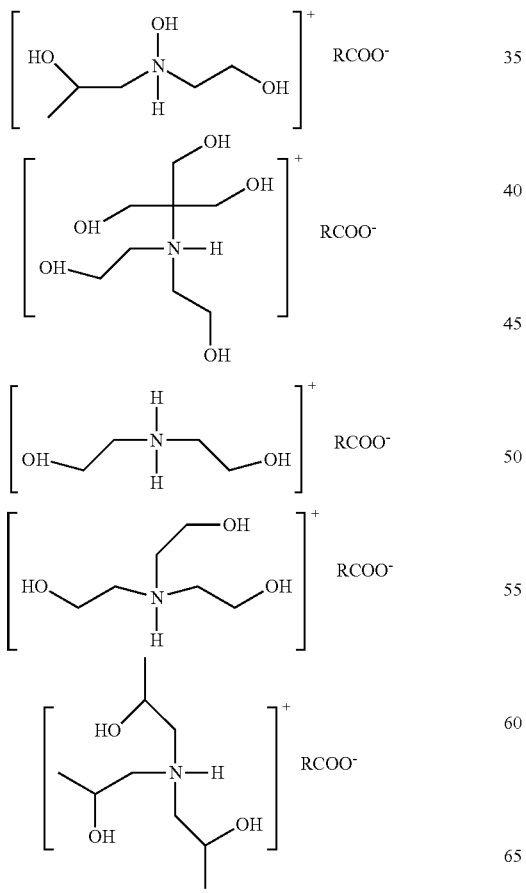

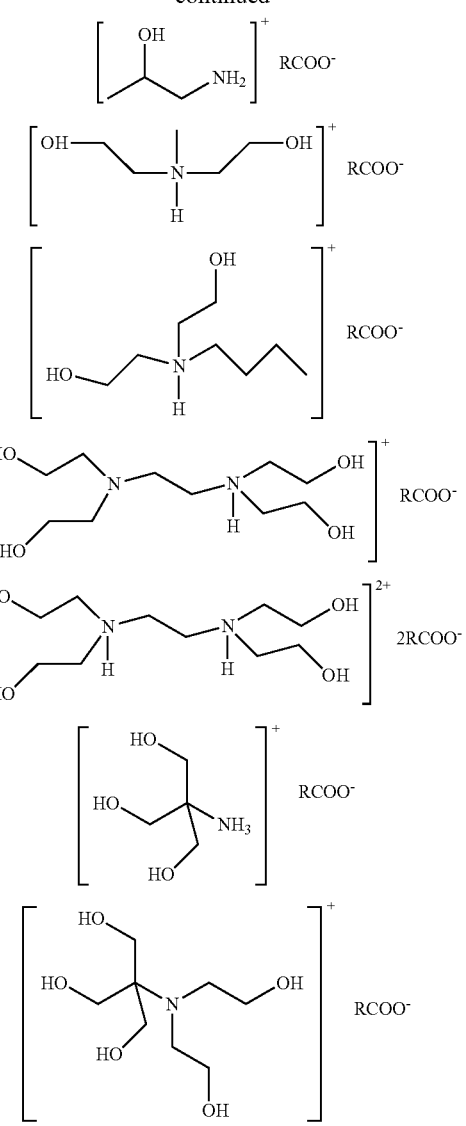

wherein R is an alkyl or alkenyl group having 3 to 9 carbon atoms, preferably pentyl or heptyl.

In especially preferred embodiments component (b) includes a salt of octanoic acid and an amine selected from triethanolamine and diethanolamine, preferably triethanolamine.

Component (b) may comprise a mixture of two or more amine salts of a carboxylic acid, suitably two or more salts in which the carboxylic acid has 4 to 10 carbon atoms.

In some preferred embodiments component (b) comprises an aldehyde, preferably an alpha-substituted aldehyde and/or a hydroxysubstituted aldehyde.

In some embodiments component (b) comprises a succinimidyl ester, preferably a compound of formula (IV).

In some preferred embodiments component (b) comprises a chelating agent, preferably a polycarboxylic acid derived chelating agent.

In some preferred embodiments component (b) comprises an amine salt of a carboxylic acid, preferably wherein the carboxylic acid has 4 to 10 carbon atoms.

In some embodiments component (b) comprises an aldehyde, preferably an alpha-substituted aldehyde and/or a hydroxysubstituted aldehyde and a chelating agent, preferably a polycarboxylic acid derived chelating agent.

In some embodiments component (b) comprises a succinimidyl ester, preferably a compound of formula (IV) and a chelating agent, preferably a polycarboxylic acid derived chelating agent.

In some embodiments component (b) comprises an aldehyde, preferably an alpha-substituted aldehyde and/or a hydroxysubstituted aldehyde and an amine salt of a carboxylic acid, preferably wherein the carboxylic acid has 4 to 10 carbon atoms.

In some embodiments component (b) comprises a succinimidyl ester, preferably a compound of formula (IV) and an amine salt of a carboxylic acid, preferably wherein the carboxylic acid has 4 to 10 carbon atoms.

In some embodiments component (b) comprises:
  a succinimidyl ester, preferably a compound of formula (IV);
  a chelating agent, preferably a polycarboxylic acid derived chelating agent; and
  an amine salt of a carboxylic acid, preferably wherein the carboxylic acid has 4 to 10 carbon atoms.

In some preferred embodiments component (b) comprises:
  an aldehyde, preferably an alpha-substituted aldehyde and/or a hydroxy substituted aldehyde;
  a chelating agent, preferably a polycarboxylic acid derived chelating agent; and
  an amine salt of a carboxylic acid, preferably wherein the carboxylic acid has 4 to 10 carbon atoms.

In some preferred embodiments component (b) comprises:
  an aldehyde selected from 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde and 2-(2-hydroxyethoxy)acetaldehyde; and
  a chelating agent selected from glutamic acid N,N-diacetic acid (GLDA), diethylene triamine pentaacetic acid (DTPA), imido disuccinic acid (IDS), L-aspartic acid, diacetic acid (ASDA), ethylene diamine tetraacetic acid (EDTA), ethylene diamine disuccinic acid (EDDS), hydroxyethyl ethylenediaminetriacetic acid (HEDTA), citric acid and mixtures thereof.

In some preferred embodiments component (b) comprises:
  an aldehyde selected from 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde and 2-(2-hydroxyethoxy)acetaldehyde; and
  an amine salt of a carboxylic acid wherein the carboxylic acid has 4 to 10 carbon atoms and the amine is compound of formula $R^1R^2R^3N$, wherein each of $R^1$, $R^2$ and $R^3$ is independently selected from hydrogen and an alkyl or hydroxyalkyl group having 1 to 6 carbon atoms, for example 1 to 4 carbon atoms.

In some preferred embodiments component (b) comprises:
  an aldehyde selected from 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde and 2-(2-hydroxyethoxy)acetaldehyde;
  a chelating agent selected from glutamic acid N,N-diacetic acid (GLDA), diethylene triamine pentaacetic acid (DTPA), imido disuccinic acid (IDS), L-aspartic acid, diacetic acid (ASDA), ethylene diamine tetraacetic acid (EDTA), ethylene diamine disuccinic acid (EDDS), hydroxyethyl ethylenediaminetriacetic acid (HEDTA), citric acid and mixtures thereof; and
  an amine salt of a carboxylic acid wherein the carboxylic acid has 4 to 10 carbon atoms and the amine is compound of formula $R^1R^2R^3N$, wherein each of $R^1$, $R^2$ and $R^3$ is independently selected from hydrogen and an alkyl or hydroxyalkyl group having 1 to 6 carbon atoms, for example 1 to 4 carbon atoms.

In some preferred embodiments component (b) comprises:
  an aldehyde selected from 2-hydroxyhexanal and 2-hydroxyoctanal and 2-hydroxypropanal;
  a chelating agent selected from glutamic acid N,N-diacetic acid (GLDA), diethylene triamine pentaacetic acid (DTPA) and mixtures thereof; and
  the diethanolamine or triethanolamine salt of octanoic acid or hexanoic acid.

In some preferred embodiments component (b) comprises 2-hydroxyoctanal and GLDA.

In some preferred embodiments component (b) comprises 2-hydroxyoctanal, GLDA and the triethanolamine salt of octanoic acid.

In some preferred embodiments component (b) comprises 2-hydroxyoctanal, GLDA and the triethanolamine salt of octanoic acid.

In some embodiments the concentrate composition of the first aspect of the present invention comprises
  (a) at least 0.1 wt % of a surfactant compound, preferably an amphoteric and/or anionic surfactant compound; and
  (b) at least 10 wt % of one or more compounds selected from
    an aldehyde selected from 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde and 2-(2-hydroxyethoxy)acetaldehyde;
    a chelating agent selected from glutamic acid N,N-diacetic acid (GLDA), diethylene triamine pentaacetic acid (DTPA), imido disuccinic acid (IDS), L-aspartic acid, diacetic acid (ASDA), ethylene diamine tetraacetic acid (EDTA), ethylene diamine disuccinic acid (EDDS), hydroxyethyl ethylenediaminetriacetic acid (HEDTA), citric acid and mixtures thereof; and
    an amine salt of a carboxylic acid wherein the carboxylic acid has 4 to 10 carbon atoms and the amine is compound of formula $R^1R^2R^3N$, wherein each of $R^1$, $R^2$ and $R^3$ is independently selected from hydrogen and an alkyl or hydroxyalkyl group having 1 to 6 carbon atoms, for example 1 to 4 carbon atoms.

In some embodiments the concentrate composition of the first aspect of the present invention comprises
  (a) at least 0.1 wt % of a surfactant compound, selected from sodium laureth sulfate and cocamido propyl betaine, and
  (b) at least 10 wt % of one or more components selected from
    an aldehyde selected from 2-hydroxyhexanal and 2-hydroxyoctanal and 2-hydroxypropanal;
    a chelating agent selected from glutamic acid N,N-diacetic acid (GLDA), diethylene triamine pentaacetic acid (DTPA) and mixtures thereof; and the diethanolamine or triethanolamine salt of octanoic acid or hexanoic acid.

The concentrated composition of the present invention comprises (a) 0.1 wt % of a surfactant compound. Preferably the composition comprises at least 0.5 wt %, preferably at least 0.8 wt %, more preferably at least 1.0 wt % of a surfactant compound. In some embodiments the composition may comprise more than 1.5 wt % or more than 2.0 wt % of the surfactant compound.

The concentrate composition of the present invention may comprise up to 20 wt % of the surfactant compound (a) preferably up to 15 wt %, suitably up to 10 wt %, preferably up to 8 wt %, for example up to 6 wt %.

Component (a) may comprise a mixture of surfactant compounds. In such embodiments the above amounts refer to the total amount of all surfactant components present in the composition.

The concentrate composition of the present invention comprises at least 10 wt % of component (b).

Preferably the concentrate composition comprises at least 12 wt % component (b), preferably at least 14 wt %, at least 15 wt %, suitably at least 17 wt %, preferably at least 18 wt %, for example at least 20 wt %.

The concentrate composition of the present invention may comprise up to 60 wt % component (b), suitably up to 55 wt %, preferably up to 50 wt % and more preferably up to 45 wt %, suitably up to 40 wt %, for example up to 35 wt %. Component (b) may comprise a mixture of compounds. In such embodiments the above amounts refer to the total of all such compounds present in the composition.

In some preferred embodiments the composition of the present invention comprises from 0.5 to 10 wt % of component (a) and from 15 to 35 wt % of component (b).

The concentrate composition of the first aspect may consist essentially of component (a), component (b) and water or may comprise one or more further ingredients, for example one or more solvents. Suitable solvents include water miscible solvents. Preferred solvents include alcohols and esters.

Preferably component (a), component (b) and water together comprise at least 80 wt % of the concentrate composition, preferably at least 85 wt %, more preferably at least 90 wt %, suitably at least 95 wt %, for example at least 98 wt % or at least 99 wt %.

Component (a) and component (b) comprise at least 10 wt % of the concentrate composition of the present invention. Preferably they comprise at least 12 wt %, preferably at least 15 wt %, more preferably at least 20 wt %

Component (b) preferably comprises an aldehyde, a chelating agent and an amine salt of a carboxylic acid.

The concentrate composition of the present invention preferably comprises at least 0.1 wt % of an aldehyde, preferably at least 0.5 wt %, more preferably at least 1 wt %, for example at least 2 wt % or at least 3 wt %.

The composition may comprise up to 30 wt % of an aldehyde, preferably up to 20 wt %, suitably up to 15 wt %, for example up to 12 wt % or up to 10 wt %.

The concentrate composition of the present invention preferably comprises at least 0.1 wt % of a chelating agent, preferably at least 1 wt %, more preferably at least 2 wt %, for example at least 3 wt %, at least 4 wt % or at least 5 wt %.

The concentrate composition may comprise up to 50 wt % chelating agent, preferably up to 40 wt %, suitably up to 30 wt %, for example up to 25 wt %.

The concentrate composition of the present invention preferably comprises at least 0.1 wt % of an amine salt of a carboxylic acid, preferably at least 0.5 wt %, more preferably at least 1 wt %, for example at least 2 wt %, at least 3 wt % or at least 4 wt %.

The concentrate composition of the present invention may comprise up to 40 wt % of an amine salt of a carboxylic acid, suitably up to 30 wt %, preferably up to 20 wt %, for example up to 17 wt %, or up to 15 wt %.

In one embodiment the concentrate composition of the present invention comprises from 0.1 to 30 wt % of an aldehyde, from 0.1 to 50 wt % of a chelating agent and from 0.1 to 40 wt % of an amine salt of a carboxylic acid.

In one embodiment the concentrate composition of the present invention comprises from 2 to 10 wt % of an aldehyde, from 5 to 25 wt % of a chelating agent and from 3 to 15 wt % of an amine salt of a carboxylic acid.

When mixtures of two of more aldehydes, chelating agents or amine salts are present, the above amounts refer to the total of all such compounds of that type present in the compositions.

The weight ratio of chelating agent:aldehyde present in component (b) is preferably at least 0.5:1, preferably at least 1:1, more preferably at least 1.2:1.

The weight ratio of chelating agent:aldehyde present in component (b) may be up to 20:1, suitably up to 10:1, for example 5:1.

The weight ratio of chelating agent:amine salt present in component (b) is preferably at least 0.5:1, preferably at least 1:1, suitably at least 1.2:1.

The weight ratio of chelating agent:amine salt present in component (b) may be up to 20:1, suitably up to 10:1, for example up to 5:1.

The weight ratio of amine salt:aldehyde is preferably at least 0.1:1, more preferably at least 0.25:1, suitably at least 0.5:1.

The weight ratio of amine salt:aldehyde may be up to 10:1, suitably up to 5:1, preferably up to 2:1.

The weight ratio of component: (b) component (a) is suitably from 100:1 to 1:1, preferably from 50:1 to 2:1, suitably from 20:1 to 3:1.

In one embodiment the concentrate composition of the present invention comprises from 0.5 to 5 wt % of a surfactant, from 2 to 10 wt % of an aldehyde, from 5 to 25 wt % of a chelating agent and from 3 to 15 wt % of an amine salt of a carboxylic acid.

The concentrate compositions of the present invention is preferably in the form of a stable emulsion. Suitably the emulsion is storage stable under ambient conditions. Suitably the emulsion does not break down during storage. It remains a single phase clear emulsion.

Preferably the composition is stable and does not break down on storing for 48 hours at 1 atmosphere and a temperature of 20 to 25° C.

Preferably the composition is stable and does not break down on storing for 1 month at 1 atmosphere and a temperature of 20 to 25° C.

Preferably the composition is stable and does not break down on storing for 4 months 1 atmosphere and a temperature of 20 to 25° C.

Preferably the composition is stable and does not break down after storing for 12 months at 1 atmosphere and a temperature of 20 to 25° C.

The present invention provides a concentrate composition comprising at least two components that is stable. This can be used in the formulation of further products.

According to a second aspect of the present invention there is provided a formulated composition comprising the concentrate composition of the first aspect and one or more further components.

According to a third aspect of the present invention there is provided a method of preparing a formulated composition, the method comprising admixing a concentrate composition of the first aspect with one or more further components.

Preferred features of the second and third aspects are suitably as defined in relation to the third aspect. Further preferred features of the invention will now be described.

The formulated composition may be any formulated product which comprises multiple ingredients of the concentrate composition.

In some embodiments the formulated composition may be a cleaning composition. For example it may be a laundry detergent composition or a carpet cleaning composition.

In some embodiments the formulated composition is a laundry detergent composition. In such embodiments the composition suitably comprises one or more further ingredients selected from builders, surfactants, chelating agents, bleaches, optical brighteners, enzymes, fragrances and other such ingredients commonly found in laundry detergent compositions. The composition may be a hand washing laundry detergent composition or an automatic laundry detergent composition.

In preferred embodiments the formulated composition is a personal care composition. Most preferably the formulated composition is a hair care composition.

The formulated composition of the second aspect of the present invention preferably provides a benefit to a material treated with it. Suitably the formulated composition enhances at least one property of a material that is treated with it.

The formulated composition of the second aspect of the present invention is preferably a hair benefit composition. Suitably it enhances at least one property of the hair.

In some embodiments the formulated composition of the second aspect may provide a temporary change to a property of the hair, for example by providing increased shine or gloss, or improved softness or combability.

A temporary change in the property of the hair may be due to the composition coating the surface of the hair but forming a weak interaction such that the composition can be easily washed or brushed away.

In some preferred embodiments the formulated composition of the second aspect may provide a longer lasting benefit to the hair, for example a wash-durable benefit.

The formulated composition may be useful in permanent waving or straightening of the hair.

The formulated composition may improve the strength of the hair.

The formulated composition may prevent or inhibit loss of protein from the hair and/or they may be used to bind extra protein to the hair.

The formulated composition may provide protection to the hair against damage. For example the composition and method of the present invention may protect against damage from heat or sunlight.

In some embodiments the formulated composition may provide chemical resistance, for example protection against chlorine and other compounds found in swimming pools and the like.

Suitably the formulated composition may enhance at least one property of hair selected from shine, gloss, softness, combability, strength, straightness, waviness, thermal durability and UV stability.

Preferably the invention provides one or more benefits selected from increased and/or permanent/semi-permanent gloss or shine, improved and/or permanent/semi-permanent combability, improved and/or permanent/semi-permanent strength, increased and/or permanent/semi-permanent softness, reduced protein loss, improved thermal durability, increased chemical resistance, permanent/semi-permanent waviness and and/or permanent/semi-permanent straightness.

The ingredients of component (b) have been advantageously found to reduce colour loss from a dyed material.

In some embodiments compositions of the present invention may be used to combat colour loss from a dyed textile material. In such embodiments the dyed textile material suitably comprises wool and preferably comprises wool as a major proportion thereof.

In particular the components have been found to combat colour loss from a dyed keratin material, for example hair, especially human or animal hair, preferably human hair.

The formulated compositions of the present invention may comprise different components depending on the intended use thereof. In some embodiments the composition may be used immediately after dyeing the hair. Alternatively the composition may be used one or more times as a hair treatment composition. In some embodiments it may be provided as a colour-loss prevention composition. Alternatively the formulated composition may be in the form of shampoo, conditioner or hair styling product, for example a serum, wax, mousse, gel or spray or any other hair treatment form that could be used to provide general hair care benefits. Formulated compositions which perform multiple functions, for example combined shampoo and conditioning compositions are also within the scope of the invention.

Suitably the formulated composition comprises one or more additional components selected from surfactants (including anionic, amphoteric, nonionic and cationic surfactants); conditioning agents (including quaternary ammonium compounds, cationic polymers, silicones, synthetic or natural oils or resins etc), fatty alcohols, electrolytes or other rheology modifiers, opacifying/pearlising agents, scalp benefit agents, fragrances, dyes, UV filters, penetration enhancers (eg, propylene carbonate, benzyl alcohol etc), preservatives, antioxidants, emulsifiers, pH adjusting agents and buffers and styling polymers (eg, polyvinylpyrrolidone, etc).

In some embodiments the formulated composition of the second aspect of the present invention is a shampoo composition.

Suitable shampoo compositions of the present invention may typically comprise 0.5 to 60 wt % of one or more anionic surfactants, preferably 1 to 50 wt %, more preferably 5 to 30 wt %, for example 8 to 20 wt % or 8 to 12 wt %; optionally from 0.1 to 30 wt % of amphoteric surfactants, preferably 1 to 15 wt %, for example 2 to 12 wt %; and optionally 0.1 to 40 wt % of non-ionic surfactants, preferably 0.5 to 30 wt %, for example 1 to 15 wt % or 2 to 12 wt %.

Shampoo compositions of the present invention may comprise one or more ingredients selected from anionic surfactants (eg, sodium laureth sulfate, sodium lauroyl methyl isethionate, sodium cocoyl methyl isethionate, sodium alpha-olefin sulfonate, sodium lauryl sulfoacetate, sodium monoalkyl phosphates, sodium dialkyl phosphates and sodium cocoyl methyl taurate, amphoteric surfactants (eg, cocamidopropyl betaine, sodium lauroamphoacetate, cocamidopropylhydroxy sultaine and disodium cocoamphodiacetate), foam boosters (eg, cocamide DEA, cocamide MEA, cocamide MIPA laureth-3), fatty alkyl alcohols (eg, cetyl alcohol, stearyl alcohol and behenyl alcohol), nonionic surfactants (eg, alkylpolyglucosides and alkyl ether ethoxylates), cationic polymers (eg, guar hydroxypropyl trimonium chloride, polyquaternium-10), silicones (eg, polydimethylsiloxanes such as dimethicone and dimethiconol), rheology modifiers (eg, carbomer, PEG-150 distearate and xanthan gum), synthetic or natural oils or resins (eg, mineral oil or vegetable oils), anti-dandruff agents (eg, piroctone olamine, zinc pyrithione and salicylic acid), styling agents (eg, polyisobutylene and polyvinyl pyrollidone/vinyl acetate copolymer), moisturising agents (eg, panthenol and glycerol), non-polymeric conditioning agents (eg, quaternary ammonium compounds such as behentrimonium chloride and stearalkonium chloride), opacifying/pearlising agents (eg, styrene/acrylates copolymer and ethylene glycol distearate), scalp benefit agents, fragrance, colouring agents, hair dyes, sunscreens, UV filters, preservatives, penetration enhancers (eg, propylene carbonate, benzyl alcohol etc) and diluents and carriers as defined herein.

Some preferred shampoo compositions of the present invention include 0.5 to 60 wt % of one or more anionic surfactants (for example, sodium laureth sulfate, sodium lauroyl methyl isethionate, sodium cocoyl isethionate, sodium alpha-olefin sulfonate, sodium lauryl sulfoacetate, sodium monoalkyl phosphates and sodium dialkyl phosphates); and 0 to 30 wt % of amphoteric surfactants (for example, cocamidopropyl betaine, sodium lauroamphoacetate and cocamidopropylhydroxy sultaine).

In some embodiments the formulated composition of the second aspect of the present invention is a conditioning composition.

Suitable conditioning compositions of the present invention may typically comprise 0.1 to 20 wt % of one or more cationic surfactants, preferably 0.5 to 8 wt %, more preferably 1 to 4 wt %; and 0.1 to 20 wt % of one or more fatty alkyl alcohols, preferably 0.5 to 8 wt %, more preferably 1 to 4 wt %; and optionally 0.1 to 20 wt % of one or more non-ionic surfactants, preferably 0.5 to 8 wt %, more preferably 1 to 4 wt %; and optionally 0.1 to 20 wt % of one or more cationic polymers, preferably 0.5 to 8 wt %, more preferably 1 to 4 wt %.

Conditioning compositions of the present invention including rinse-off and leave-on conditioners (including 'hair masks') and hair shine or appearance enhancing products, anti-frizz treatment serums and other treatments, either leave-in or rinse-off, designed to be applied to the hair immediately after colouring or any time thereafter, and hair-tonics. Such compositions may comprise one or more further ingredients selected from: cationic surfactants including mono- and di-fatty alkyl tertiary amines and quaternary ammonium compounds (eg, mono- and di-fatty alkyl quaternary ammonium compounds, such as cetrimonium chloride, steartrimonium chloride and behentrimonium chloride), fatty alkyl alcohols (eg, cetyl alcohol, stearyl alcohol and behenyl alcohol), nonionic surfactants (eg, alkylpolyglucosides and alkyl ether ethoxylates, eg, ceteareth-20), cationic polymers (eg, guar hydroxypropyl trimonium chloride, polyquaternium-10), silicones (eg, polydimethylsiloxanes such as dimethicone and dimethiconol), rheology modifiers (eg, hydroxyethyl cellulose and polyquaternium-37), moisturising agents (eg, panthenol and glycerol), non-polymeric conditioning agents (eg, quaternary ammonium compounds such as behentrimonium chloride and stearalkonium chloride), scalp benefit agents, fragrance, colouring agents, hair dyes, sunscreens, UV filters preservatives, penetration enhancers (eg, propylene carbonate, benzyl alcohol etc), and diluents and carriers as defined herein.

Some preferred conditioning compositions of the present invention include 0.1 to 20 wt % of cationic surfactants (for example mono- and di-fatty alkyl quaternary ammonium compounds, mono- and di-fatty alkyl tertiary amines), 0.1 to 20 wt % of fatty alkyl alcohols; and 0.1 to 20 wt % of non-ionic surfactants (for example ceteareth-20).

In some embodiments the formulated composition of the second aspect of the invention is a hair styling composition.

Suitable hair styling compositions of the present invention may typically comprise from 0.1 to 40 wt % of one or more hair styling polymers, preferably from 0.1 to 30 wt %, more preferably from 0.5 to 10 wt %.

Hair styling compositions of the present invention (including gels, mousses with and without propellant, hair sprays with and without propellant, hair pomades, hair waxes, hair creams, hair brilliantines and compositions designed to be used in conjunction with heated styling appliances such as blow dryers, curling tongs, straightening irons, hot air hoods (as used for example in hair salons)) may comprise one or more further ingredients selected from: hair styling polymers (eg, polyvinylpyrrolidone, polyvinylpyrrolidone/vinyl acetate copolymers, octylacrylamide/acrylates/butylaminoethyl methacrylate copolymer, methyl vinyl ether/maleic anhydride copolymers and polyethylene waxes), rheology modifiers (eg, carbomers, acrylates copolymers, hydroxyethylcellulose, xanthan gum and polyquaternium-37), aminomethyl propanol, fatty alkyl alcohols (eg, cetyl alcohol, stearyl alcohol and behenyl alcohol), ethanol, propyl alcohol, isopropyl alcohol, petrolatum, mineral oil, ozokerite, beeswax, carnauba wax, silicones (eg, polydimethylsiloxanes such as dimethicone and dimethiconol), polyethylene glycols, anionic surfactants (eg, sodium laureth sulfate and sodium lauroyl methyl isethionate), amphoteric surfactants (eg, cocamidopropyl betaine and disodium cocoamphodiacetate), nonionic surfactants (eg, alkylpolyglucosides and alkyl ether ethoxylates), cationic polymers (eg, guar hydroxypropyl trimonium chloride, polyquaternium-10), silicones (eg, polydimethylsiloxanes such as dimethicone and dimethiconol), moisturising agents (eg, panthenol and glycerol), non-polymeric conditioning agents (eg, quaternary ammonium compounds such as behentrimonium chloride and stearalkonium chloride), scalp benefit agents, fragrance, colouring agents, hair dyes, sunscreens, UV filters, preservatives, penetration enhancers (eg, propylene carbonate, benzyl alcohol, etc), and diluents and carriers as defined herein.

Some preferred hair styling compositions of the present invention include 0.1 to 40 wt % of one or more hair styling polymers/resins (for example, polyvinylpyrrolidone, polyvinylpyrrolidone/vinyl acetate copolymers, octylacrylamide/acrylates/butylaminoethyl methacrylate copolymer, methyl vinyl ether/maleic anhydride copolymers and polyethylene waxes).

Those skilled in the art will appreciate that it is possible to confer one or more attributes of hair conditioning, shine etc, and hair styling to the hair from a single product containing the appropriate ingredients thus compositions having such combinations of hair benefit effects are also covered in the invention.

In some embodiments the formulated composition of the second aspect is a hair permanent waving composition.

Suitable hair permanent waving compositions of the present invention may typically comprise 0.1 to 20 wt % of one or more reducing agents, preferably from 0.5 to 15 wt %, more preferably 3 to 12 wt %.

Some preferred hair permanent waving compositions of the present invention include 0.5 to 15 wt % of one or more reducing agents (for example, as thioglycolic acid, ammonium thioglycolate, thiolactic acid, cystamine, cysteine, glycerol monothioglycolate, sodium sulfite/bisulfite); alkalising agents (for example, ammonia, monoethanolamine) in an amount sufficient to adjust the pH of the reducing component to between pH 8-13. Hair permanent waving compositions are typically provided in a package with a second composition comprising 0.5 to 10 wt % of one or more oxidising agents (for example, hydrogen peroxide, sodium bromate, sodium percarbonate and sodium perborate) which are applied after the reducing agent composition has been applied, allowed to process and then rinsed off.

In some embodiments the formulated composition of the second aspect of the present invention is a hair relaxing composition.

Hair relaxing compositions of the present invention may include one or more ingredients selected from sodium hydroxide, lithium hydroxide, potassium hydroxide, calcium hydroxide and guanidine carbonate. These components are suitably present in an amount of from 0.5 to 5 wt %.

Other types of permanent straightening compositions may include one or more ingredients selected from formaldehyde, glyoxylic acid, glutaraldehyde and glyoxyloyl carbocysteine. These components are suitably present in an amount of from 0.1 to 10 wt %.

The hair permanent waving, relaxing and permanent straightening compositions mentioned above may further include one or more additional ingredients selected from anionic surfactants (eg, sodium laureth sulfate and sodium lauroyl methyl isethionate), amphoteric surfactants (eg, cocamidopropyl betaine and disodium cocoamphodiacetate), quaternary ammonium compounds (eg, cetrimonium chloride, steartrimonium chloride and behentrimonium chloride), fatty alkyl alcohols (eg, cetyl alcohol, stearyl alcohol and behenyl alcohol), nonionic surfactants (eg, alkylpolyglucosides and alkyl ether ethoxylates), cationic polymers (eg, guar hydroxypropyl trimonium chloride, polyquaternium-10), silicones (eg, polydimethylsiloxanes such as dimethicone and dimethiconol), opacifying agents (eg, styrene acrylates copolymer), rheology modifiers (eg, hydroxyethyl cellulose and xanthan gum), moisturising agents (eg, panthenol and glycerol), non-polymeric conditioning agents (eg, quaternary ammonium compounds such as behentrimonium chloride and stearalkonium chloride), fragrance, sunscreens, UV filters, colouring agents and diluents and carriers as defined herein.

In some embodiments the formulated composition of the second aspect of the present invention is a hair colouring composition.

Hair colouring compositions may include a dye compound and/or may include a dye precursor compound which forms an active dye in the hair in situ following admixture with an oxidising composition.

Oxidative hair colouring compositions of the present invention may include one or more intermediates, for example p-phenylenediamine, N,N-bis(2-hydroxyethyl)-p-phenylenediamine, p-toluenediamine, p-aminophenol, phenyl methyl pyrazolone, m-phenylenediamine, resorcinol, 1-naphthol, 1-hydroxyethyl 4,5-diamino pyrazole and m-aminophenol. These intermediates can be present in any combination and ratios at a total intermediate concentration of from 0.01 to 15% depending upon the desired shade. Such compositions typically further include one or more alkalising agents, for example ammonia, ammonium hydroxide, sodium hydroxide and monoethanolamine. Developer compositions for oxidative dyeing include an oxidising agent, for example hydrogen peroxide, sodium bromate, sodium percarbonate or sodium perborate. These are typically present in an amount of from 0.1 to 30 wt %.

Direct-dye colour compositions of the present invention may include one of more direct dyes for example from the classes of nitrophenylenediamines (eg, 4-nitro-o-phenylenediamine etc), nitroaminophenols (eg, 2-amino-4-nitrophenol etc), aminoanthraquinones (eg, Disperse Red 11 etc). These are typically present in an amount of 0.1 to 20 wt %, depending on the desired shade.

In some preferred embodiments the formulated composition of the second aspect of the present invention is not a hair colouring composition. Preferably the composition comprises less than 0.1 wt %, preferably less than 0.01 wt % of dye compounds and/or dye precursor compounds. Preferably the composition does not comprise dye compounds and/or dye precursor compounds. Compounds which provide colour to the composition such as pigments and pearlescent agents may be present but suitably the composition does not include any compounds which may be used to dye hair.

According to a fourth aspect of the present invention there is provided the use of a concentrate composition of the first aspect or a formulated composition of the second aspect to combat colour loss from a dyed material.

By combating colour loss we mean to include reducing the loss of colour from a dyed material and/or preventing or inhibiting the loss of colour from a dyed material, for example dyed hair.

The invention will now be further described with reference to the following non-limiting examples.

EXAMPLE 1

Compositions were prepared comprising the following components:

| | Wt % as active in formulation |||||||||
|---|---|---|---|---|---|---|---|---|---|
| | Formulation |||||||||
| | 1 | 2 | 3 | 4 | 5 | 6 | 7 | 8 | 9 |
| Na$_4$ GLDA[1] | 16.7 | 20.0 | 13.4 | 16.7 | 16.7 | 20.0 | 16.7 | 20.0 | 23.4 |
| 2 hydroxy octanal | 5.0 | 6.0 | 4.0 | 5.0 | 5.0 | 6.0 | 5.0 | 6.0 | 7.0 |
| Triethanolamine salt of octanoic acid | 7.5 | 9.0 | 6.0 | 7.5 | 7.5 | 9.0 | 7.5 | 9.0 | 10.5 |

-continued

| | Wt % as active in formulation | | | | | | | | |
|---|---|---|---|---|---|---|---|---|---|
| | Formulation | | | | | | | | |
| | 1 | 2 | 3 | 4 | 5 | 6 | 7 | 8 | 9 |
| CAPB[2] | 0.0 | 0.0 | 1.5 | 2.3 | 2.8 | 3.3 | 3.3 | 4.0 | 4.6 |
| Water | QS to 100 wt % | | | | | | | | |

[1]Added as Dissolvine GL-38 (38 wt % $Na_4$ GLDA)
[2]Added as Empigen BS/H50 (35 wt % cocoamidopropyl betaine)

EXAMPLE 2

Formulations 1 to 9 were stored for 48 hours at 25° C. and visually assessed. A stable system was a clear single phase.
Formulations 1 and 2 were unstable after 48 hours whereas formulations 3 to 9 were all stable.

EXAMPLE 3

Formulation 7 was stored for 4 months under ambient conditions (20-25° C., 1 atm). It remained stable after this period.

The invention claimed is:

1. A concentrate emulsion composition consisting of water and:
   (a) from 0.1 to 10 wt % of an amphoteric and/or anionic surfactant compound;
   (b) from 2 to 10 wt % of 2-hydroxyoctanal;
   (c) from 5 to 25 wt % of glutamic acid N,N-diacetic acid (GLDA); and
   (d) from 3 to 15 wt % of a triethanolamine salt of octanoic acid;
   wherein said emulsion composition is storage stable under ambient conditions for at least 48 hours without breaking down.

2. The concentrate emulsion composition according to claim 1 wherein the amphoteric and/or anionic surfactant compound is selected from the group consisting of sodium laureth sulfate (SLES), cocamidopropyl betaine (CAPB), and mixtures thereof.

3. The concentrate emulsion composition according to claim 1 wherein the amphoteric and/or anionic surfactant compound comprises cocamidopropyl betaine (CAPB).

4. The concentrate emulsion composition according to claim 1 wherein component (a) and combined components (b), (c) and (d) together are between 20 and 60 wt % of the composition.

5. A method of preparing a formulated composition, the method comprising admixing the concentrate composition as defined in claim 1 with one or more further components.

6. The method according to claim 5 wherein the formulated composition is a hair care composition.

7. The method according to claim 6 which provides one or more benefits selected from the group consisting of increased gloss or shine, improved combability, improved strength, increased softness, reduced protein loss, improved thermal durability, increased chemical resistance, increased waviness and increased straightness; wherein the benefit may be temporary, semipermanent or permanent.

* * * * *